United States Patent [19]

Smith et al.

[11] Patent Number: 5,045,284

[45] Date of Patent: Sep. 3, 1991

[54] FLOW CELL FOR PRECIPITATION TITRATION FLOW INJECTION ANALYSIS

[75] Inventors: David D. Smith, Baton Rouge; Gary D. Deleo, Donaldsonville, both of La.

[73] Assignee: The Dow Chemical Company, Midland, Mich.

[21] Appl. No.: 274,581

[22] Filed: Nov. 22, 1988

[51] Int. Cl.⁵ ............................................. G01N 31/02
[52] U.S. Cl. ........................................ 422/81; 422/75; 436/52; 436/124; 436/150
[58] Field of Search .................. 422/81, 82.01, 82.03, 422/98, 75, 82; 436/49-52, 124, 150; 73/863.21, 863.41, 863.43; 204/153.13, 153.23

[56] References Cited

U.S. PATENT DOCUMENTS

| | | | |
|---|---|---|---|
| 3,028,225 | 4/1962 | Sheen | 422/81 |
| 3,449,233 | 6/1969 | Morrow | 204/153.13 |
| 3,770,608 | 11/1973 | Kelch et al. | 204/153.13 |
| 3,838,011 | 9/1974 | Hagen et al. | 436/52 |
| 3,875,022 | 4/1975 | Gilbert | 204/153.13 |
| 4,640,821 | 2/1987 | Mody et al. | 436/150 |
| 4,732,861 | 3/1988 | Sinclair et al. | 422/98 |
| 4,798,803 | 1/1989 | Wolcott et al. | 436/52 |
| 4,861,555 | 8/1989 | Mowery, Jr. | 436/150 |
| 4,935,106 | 6/1990 | Liston et al. | 204/403 |

OTHER PUBLICATIONS

D. Betteridge, *Analytical Chemistry*, 50, p. 832A (Aug. 1978).

*Primary Examiner*—Robert J. Warden
*Assistant Examiner*—D. John Griffith, Jr.
*Attorney, Agent, or Firm*—Timothy S. Stevens

[57] ABSTRACT

A flow injection analysis flow cell suitable for precipitation titration flow injection analysis wherein the flow cell has a chamber and a dammed space within the chamber. The carrier containing the precipitate is flowed into the dammed space and overflows it into the chamber. The flow cell is designed so that a chemical sensing probe can be inserted into the dammed space to allow precipitation titration flow injection analysis with reduced problems of flow cell plugging.

3 Claims, 1 Drawing Sheet

FLOW CELL FOR PRECIPITATION TITRATION FLOW INJECTION ANALYSIS

FIELD OF THE INVENTION

This invention is in the filed of flow cells for flow injection analysis.

BACKGROUND OF THE INVENTION

Flow injection analysis (FIA) is an important chemical analysis method which is described, for example, in the book *Flow Injection Analysis* by Ruzicka and Hansen, 1981, Wiley Publishers, New York, and by the many publications and patents naming Hansen and Ruzicka as authors and inventors, and in the extensive publications and patents of others. There are many variations of FIA, but basically a carrier liquid is flowed sequentially through a sample injector, an in-line mixer and a detector. A preselected volume of sample is injected into the carrier stream by the injector. The in-line mixer is usually simply a coil of tubing so that the injected sample is dispensed into the carrier in a controlled manner. The carrier is usually premixed with a reagent which can react with a component of interest of the sample to produce a reaction product that is sensed as a "peak" by the detector. The detector is usually a photometer based system having a flow cell through which light is shown to detect the reaction product. Chemical sensing probes such as pH electrodes and ion specific electrodes have also been used to detect the reaction product: by immersing the probe in a stirred chamber into which the carrier stream from the mixer is fed; by channeling the carrier stream from the mixer across an active portion of the probe; and by flowing a film of the carrier stream from the mixer across an active portion of the probe.

If the reaction product is a precipitate, then FIA is often unsuccessful because the precipitate tends to clog the detector portion of an FIA system with deposits of the precipitate. This problem is especially apparent with extended use. As a solution to this problem, some workers periodically or continuously added precipitate dissolving chemicals to the carrier stream. However, some precipitates are difficult to dissolve. As a rule, precipitation reactions in FIA have not been widely used because of the above-mentioned problems and it would be an advance for FIA if a detection flow cell was designed so as to allow extended use for precipitation reactions without the need for precipitate dissolving chemicals.

SUMMARY OF THE INVENTION

The present invention is a solution to the above-mentioned problems with precipitation reactions in FIA. The present invention comprises a housing which has at least side wall and bottom wall portions to define a cavity. The housing can also have a perforated top wall. Positioned within this cavity is an overflow dam. This dam defines a contained space so that a suspension of particles in a liquid, i.e., the precipitate in the carrier, flowed into the space by a first conduit means, fills it and then overflows the dam into the cavity of the housing from which it is removed through a second conduit means positioned in or near the bottom wall of the housing. The above-mentioned optional perforated top wall, if used, has its perforation aligned with the contained space of the dam so that a chemical sensing probe can be inserted through the perforation into the contained space. The chemical sensing probe can be a chloride ion specific electrode.

DETAILED DESCRIPTION OF THE INVENTION

Figure 1:
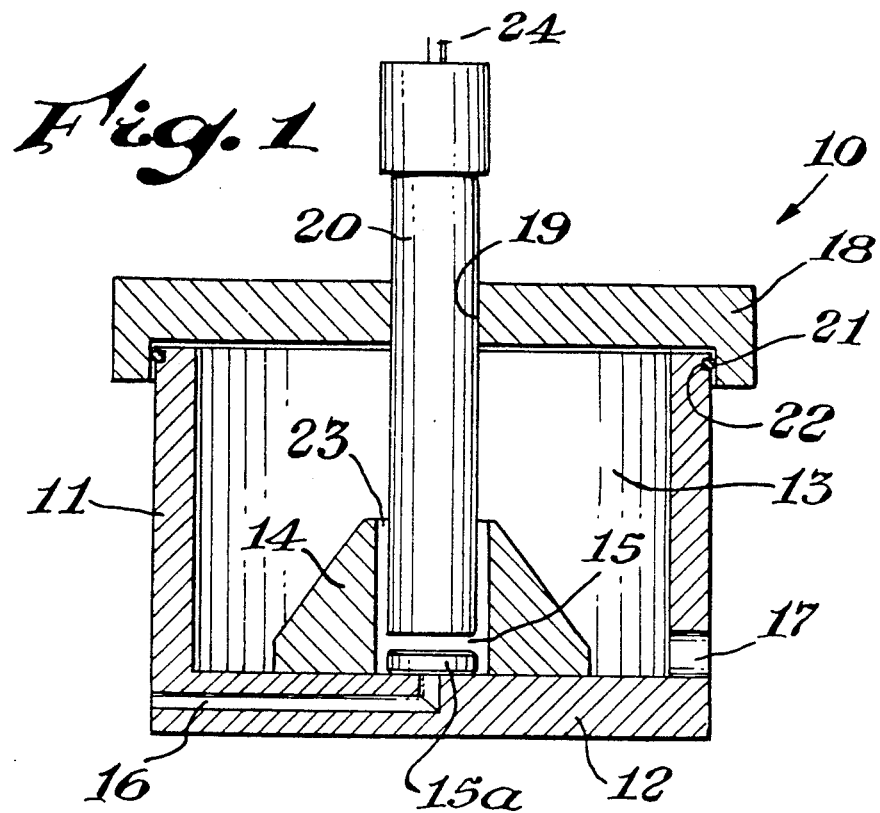
FIG. 1 is a cross-sectional view of a preferred embodiment of a flow cell according to the present invention showing an interior dammed space into which is positioned a chemical sensing probe.

Referring now to FIG. 1, therein is shown a preferred flow cell 10 of the present invention. The flow cell 10 incorporates a housing having a side wall portion 11 and a bottom wall portion 12 which define a cavity 13. Within the cavity 13 is positioned a dam 14 defining a contained space 15 so that a suspension of solid particles in a liquid flowed into the space 15, via a first conduit means or channel 16, fills the space 15 and then overflows the dam 14 into the cavity 13. The suspension of solid particles in a liquid that overflows the dam 14 into the cavity 13 is flowed therefrom via a second conduit means or channel 17 positioned near the bottom wall portion 12.

The flow cell 10 is also shown having a cover or top wall portion 18. The top wall portion 18 has a hole or perforation 19 aligned with the space 15 so that a chemical sensing probe 20 is positioned through the perforation 19 into the space 15. An 0-ring 21 contained in a grove or gland 22 is provided to retain the top wall portion 18 to the side wall portion 11, i.e., it is not critical in the present invention that the top wall portion 18 be sealed to the side wall portion 11. The dam 14 is shown as a hollow conical ring which can be attached to the bottom wall 12, if desired, by suitable means such as by an adhesive agent or by screws. Alternatively, the dam 14 can be integrally machined with the bottom wall 12. It should be understood that it is not critical that the dam 14 be attached to the bottom wall portion 12. The channel 17 should be positioned at or near the bottom wall portion 12 so that solids tend to flow out of the bottom of the chamber 13 rather than settle there.

The probe 20 is shown as having a friction slip fit in the perforation 19 but it can be held in place otherwise if desired such as by a collar and nut. The gap 23 between the dam 14 and the probe 20 most preferably is about 0.05 inches. A substantially smaller gap than this has a tendency to plug with solids. A substantially larger gap than this can reduce sensitivity by increasing the volume of the space 15. A magnetic stirring bar 15a is provided to stir the contents of the space 15. Generally, about ⅛ of an inch clearance is provided between the probe 20 and the stirring bar 15a but this dimension is not critical in the present invention. The probe 20 is provided with an electrical cable 24 so that the probe 20 can communicate with an electrical device such as a pH meter.

Preferably, the flow cell 10 is made of plastic and most preferably of clear Plexiglas ® brand plastic. One suitable size for the flow cell 10 is to make its outside diameter and height about 3 inches, the diameter of the channel 16 about 1/16 inch, and the diameter of the channel 17 about ¼ to ½ inch.

Figure 2:
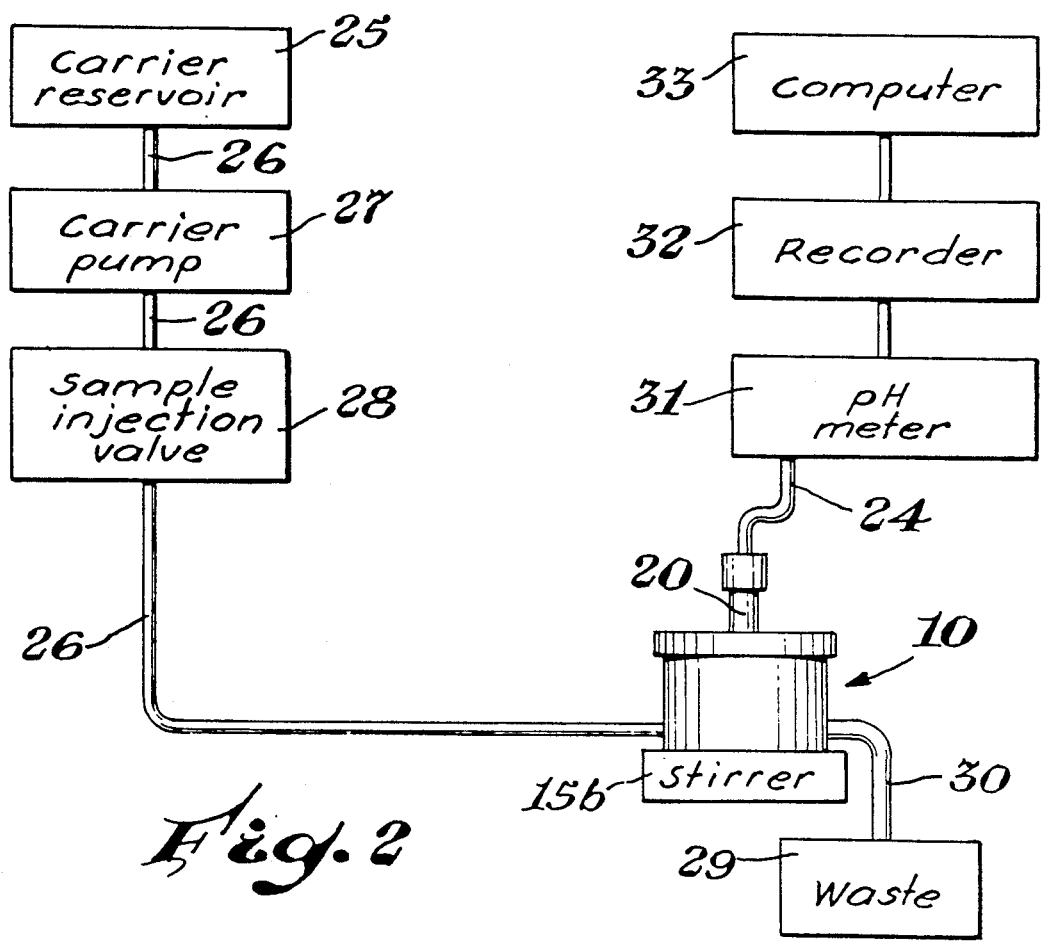
FIG. 2 is a schematic drawing of a flow injection analysis system incorporating the flow cell of FIG. 1.

Referring now to FIG. 2, therein is shown a schematic drawing of an otherwise conventional Flow Injection Analysis system incorporating the flow cell 10 of FIG. 1. A carrier reservoir 25 contains a liquid carrier which is flowed through tubing 26 and a sample injection valve 28 by a carrier pump 27 to the channel 16 of the flow cell 10. Liquid following from the channel 17 of the flow cell 10 flows to waste 29 via a pipe 30. A magnetic stirrer 15b is provided to rotate the magnetic stirring bar 15a. The probe 20 is connected to a pH meter 31 via the cable 24. A strip chart recorder 32 records the output of the pH meter 31 and a digital computer 33 can be used for quantitation and other data manipulations as is well understood in the art.

The following example is presented to illustrate the present invention. It should not be construed as limiting it in any way.

EXAMPLE 1

The system shown in FIG. 2 is assembled using: 1/16 inch Teflon ® tubing 26; ¼ inch Teflon ® tubing 30; an Orian model 96-178 solid state combination chloride ion-specific electrode probe 20; a Markson model 93 pH meter 31; a Cole-Parmer model V-8380 strip chart recorder 32;/no computer 33; a FMI model RH-ICKC carrier pump 27 set to pump at 4 ml per minute; a Rheodyne model SO 310 Teflon ® rotary sample injection valve 28 with a 50 microliter sample volume loop; a Spin-Bar brand magnetic stirring bar 15a with fins removed (Bel-Art Products, Tequannock N.J.); a Thermolyne magnetic stirrer 15b; and the flow cell shown in FIG. 1 manufactured from clear Plexiglas ® brand plastic with the dam 14 integrally machined with the bottom wall 12. The carrier contained in the reservoir 25 is water containing 0.1N $NaNO_3$; 0.16N $HNO_3$; 0.02N $AgNo_3$; and, 0.005% Zonyl ® brand type R fluorosurfactant (E.I. Dupont). The length of tubing 26 between the sample injection valve 28 and the flow cell 10 is as short as possible, i.e., about two inches, so that as much as possible of the precipitation occurs within the space 15.

The pH meter 31 reads about +300 millivolts from the probe 20 and the recorder 32 plots a substantially steady baseline at this value. The probe 20 is responding to the silver ion concentration of the carrier. When a sample is injected that contains chloride ion, it reacts with the silver ions to form silver chloride precipitate in the space 15 and thus reduces the concentration of silver ions in the carrier. When this reduction in the concentration of silver ions passes the probe 20, then its output becomes less than +300 millivolts and over time the recorder 32 thus traces a negative "peak" for an injection of a sample containing a detectable concentration of chloride ion. The log of the concentration of chloride ion in an injected standard is directly related to the width of this "peak" within a percent NaCl range of from 2.5 percent to 15 percent with a correlation coefficient of 0.99998, an intercept of −0.0038 and a slope of 0.01797, i.e., Log percent NaCl=(peak width time in seconds×0.01797)−0.0038. Replicate analyses of a process wastewater sample, manually titrated to have a percent NaCl value of 2.44, result in a mean percent NaCl value using the present system of 2.55 with a precision of 2.5 percent relative at the 95 percent confidence level. The detection limit of the system is about 1 percent NaCl which can be lowered by reducing the concentration of silver ion in the carrier.

What is claimed is:

1. A flow injection analysis flow cell suitable for precipitation titration flow injection analysis, comprising:
   (a) a housing, the housing having at least side wall, bottom wall and top wall portions which define a cavity, the top wall being perforated by a perforation;
   (b) an overflow dam positioned within the cavity, the dam defining a contained space so that a suspension of solid particles in a liquid flowed into the space fills it and then overflows the dam into the cavity of the housing, the contained space of the dam being aligned with the perforation;
   (c) a first conduit means for conducting a suspension of solid particles in a liquid into the contained space of the dam;
   (d) a second conduit means positioned in or adjacent the bottom wall portion of the housing for conducting any suspension of solid particles in a liquid that overflows the dam from the cavity of the housing to the exterior of the housing; and
   (e) a chemical sensing probe positioned through the perforation in the top wall of the housing and in the contained space of the dam so that there is a gap between the chemical sensing probe and the dam, the gap being about 0.05 inches.

2. The flow cell of claim 1 wherein the contained space of the dam is defined partially by the bottom wall portion of the housing and the first conduit means is a port through the bottom wall portion of the housing.

3. The flow cell of claim 1 wherein the chemical sensing probe is a chloride ion specific electrode.

* * * * *